(12) United States Patent
Hench et al.

(10) Patent No.: US 10,545,104 B2
(45) Date of Patent: Jan. 28, 2020

(54) COMPUTATIONALLY EFFICIENT X-RAY BASED OVERLAY MEASUREMENT

(71) Applicant: KLA-Tencor Corporation, Milpitas, CA (US)

(72) Inventors: John Hench, Los Gatos, CA (US); Andrei V. Shchegrov, Campbell, CA (US); Michael S. Bakeman, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 228 days.

(21) Appl. No.: 15/141,453

(22) Filed: Apr. 28, 2016

(65) Prior Publication Data
US 2016/0320319 A1    Nov. 3, 2016

Related U.S. Application Data

(60) Provisional application No. 62/154,108, filed on Apr. 28, 2015.

(51) Int. Cl.
*G01N 23/207*    (2018.01)

(52) U.S. Cl.
CPC ..... *G01N 23/207* (2013.01); *G01N 2223/611* (2013.01)

(58) Field of Classification Search
CPC . G01B 15/00; G01B 2210/56; G03F 7/70608; G03F 7/70616; G03F 7/70633
See application file for complete search history.

(56) References Cited

U.S. PATENT DOCUMENTS

| | | |
|---|---|---|
| 5,608,526 A | 3/1997 | Piwonka-Corle et al. |
| 5,859,424 A | 1/1999 | Norton et al. |

(Continued)

FOREIGN PATENT DOCUMENTS

| | | |
|---|---|---|
| CN | 101903832 A | 12/2010 |
| CN | 104520982 A | 4/2015 |

OTHER PUBLICATIONS

R.L. Jones, et al., "Cross Section and Critical Dimension Metrology in Dense High Aspect Ratio Patterns With CD-SAXS," AIP Conference Proceedings, vol. 788, pp. 403-406 (2005).

(Continued)

*Primary Examiner* — David J Makiya
*Assistant Examiner* — Soorena Kefayati
(74) *Attorney, Agent, or Firm* — Spano Law Group; Joseph S. Spano

(57) ABSTRACT

Methods and systems for performing overlay and edge placement errors of device structures based on x-ray diffraction measurement data are presented. Overlay error between different layers of a metrology target is estimated based on the intensity variation within each x-ray diffraction order measured at multiple, different angles of incidence and azimuth angles. The estimation of overlay involves a parameterization of the intensity modulations of common orders such that a low frequency shape modulation is described by a set of basis functions and a high frequency overlay modulation is described by an affine-circular function including a parameter indicative of overlay. In addition to overlay, a shape parameter of the metrology target is estimated based on a fitting analysis of a measurement model to the intensities of the measured diffraction orders. In some examples, the estimation of overlay and the estimation of one or more shape parameter values are performed simultaneously.

20 Claims, 9 Drawing Sheets

(56) References Cited

U.S. PATENT DOCUMENTS

| | | |
|---|---|---|
| 6,429,943 B1 | 8/2002 | Opsal et al. |
| 6,633,831 B2 | 10/2003 | Nikoonahad et al. |
| 6,734,967 B1 | 5/2004 | Piwonka-Corle et al. |
| 6,816,570 B2 | 10/2004 | Janik et al. |
| 6,895,075 B2 | 5/2005 | Yokhin et al. |
| 6,972,852 B2 | 12/2005 | Opsal et al. |
| 6,982,793 B1 * | 1/2006 | Yang ................... G03F 7/70633 356/401 |
| 7,478,019 B2 | 1/2009 | Zangooie et al. |
| 7,481,579 B2 | 1/2009 | Yokhin et al. |
| 7,616,313 B2 | 11/2009 | Kandel et al. |
| 7,826,071 B2 | 11/2010 | Shchegrov et al. |
| 7,929,667 B1 | 4/2011 | Zhuang et al. |
| 7,933,026 B2 | 4/2011 | Opsal et al. |
| 8,520,212 B2 * | 8/2013 | Coene .................... G01N 21/55 356/445 |
| 8,879,073 B2 | 11/2014 | Madsen et al. |
| 8,908,830 B2 * | 12/2014 | Omote ................... G01B 15/04 378/86 |
| 9,588,066 B2 * | 3/2017 | Pois ...................... G01N 23/201 |
| 2003/0002620 A1 * | 1/2003 | Mazor .................. G01N 23/223 378/49 |
| 2004/0038455 A1 * | 2/2004 | Seligson ................. G03F 7/705 438/122 |
| 2006/0133570 A1 | 6/2006 | Mazor et al. |
| 2007/0224518 A1 * | 9/2007 | Yokhin ............... G03F 7/70633 430/5 |
| 2008/0273662 A1 * | 11/2008 | Yun ..................... G01N 23/201 378/74 |
| 2009/0296058 A1 * | 12/2009 | Slotboom ........... G03F 7/70516 355/53 |
| 2010/0328655 A1 | 12/2010 | Boef et al. |
| 2011/0032535 A1 * | 2/2011 | Liesener ............ G03F 7/70633 356/511 |
| 2011/0276319 A1 | 11/2011 | Madsen et al. |
| 2012/0014508 A1 * | 1/2012 | Wormington ........ G01N 23/207 378/71 |
| 2012/0051518 A1 * | 3/2012 | Omote ..................... G21K 1/06 378/86 |
| 2012/0069326 A1 * | 3/2012 | Colonna de Lega ........................ G01B 11/0675 356/73 |
| 2012/0086940 A1 * | 4/2012 | Shih ..................... G01N 21/211 356/307 |
| 2013/0077742 A1 | 3/2013 | Schueler et al. |
| 2013/0155406 A1 * | 6/2013 | Den Boef ........... G03F 7/70633 356/401 |
| 2013/0304424 A1 | 11/2013 | Bakeman et al. |
| 2013/0342831 A1 | 12/2013 | Levinski et al. |
| 2014/0019097 A1 | 1/2014 | Bakeman et al. |
| 2014/0111791 A1 | 4/2014 | Manassen et al. |
| 2014/0172394 A1 | 6/2014 | Kuznetsov et al. |
| 2014/0222380 A1 | 8/2014 | Kuznetsov et al. |
| 2014/0297211 A1 | 10/2014 | Pandev et al. |
| 2015/0032398 A1 | 1/2015 | Peterlinz et al. |
| 2015/0110249 A1 | 4/2015 | Bakeman et al. |
| 2015/0117610 A1 * | 4/2015 | Veldman ............. G03F 7/70633 378/71 |
| 2015/0142395 A1 * | 5/2015 | Cao ....................... G01B 11/24 703/1 |
| 2015/0153165 A1 * | 6/2015 | Liu ...................... G01B 11/245 356/369 |
| 2015/0153657 A1 * | 6/2015 | Danilin ............... G03F 7/70516 355/52 |
| 2015/0331336 A1 * | 11/2015 | Quintanilha ........ G03F 7/70683 355/77 |
| 2015/0346605 A1 * | 12/2015 | Den Boef ............... G03F 7/705 438/401 |
| 2016/0003609 A1 | 1/2016 | Shchegrov et al. |
| 2016/0011523 A1 * | 1/2016 | Singh ................... G01J 3/2823 355/77 |
| 2016/0223476 A1 * | 8/2016 | Quintanilha ........ G03F 7/70591 |
| 2016/0282282 A1 * | 9/2016 | Quintanilha ....... G01N 21/8806 |
| 2016/0334715 A1 * | 11/2016 | Smilde ................ G03F 7/70625 |
| 2017/0010541 A1 * | 1/2017 | Mossavat ............ G03F 7/70625 |
| 2017/0031246 A1 * | 2/2017 | Den Boef ............ G01B 11/272 |
| 2017/0176871 A1 * | 6/2017 | Van Buel .............. G01N 21/93 |

OTHER PUBLICATIONS

International Search Report dated Jul. 21, 2016, for PCT Application No. PCT/US2016/029876 filed Apr. 28, 2016 by KLA-Tencor Corporation, 3 pages.

Written Opinion of the International Searching Authority dated Jul. 21, 2016, for PCT Application No. PCT/US2016/029876 filed Apr. 28, 2016 by KLA-Tencor Corporation, 3 pages.

Ko, Chun-Hung and Ku, Yi-Sha, Overlay measurement using angular scatterometer for the capability of integrated metrology. Jun. 26, 2006, vol. 15, No. 13 Optics Express 6001.

Microfabrication Technology, No. 1, 2001, 1003-8213(2001) 01-0014-05, China Academic Journal Electronic Publishing House.

* cited by examiner

COMPUTATIONALLY EFFICIENT X-RAY BASED OVERLAY MEASUREMENT

CROSS REFERENCE TO RELATED APPLICATION

The present application for patent claims priority under 35 U.S.C. § 119 from U.S. provisional patent application Ser. No. 62/154,108, entitled "Model-Free Method and Apparatus for Measuring Semiconductor Device Overlay Using X-ray Metrology Techniques," filed Apr. 28, 2015, the subject matter of which is incorporated herein by reference in its entirety.

TECHNICAL FIELD

The described embodiments relate to metrology systems and methods, and more particularly to methods and systems for improved measurement accuracy.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. A number of metrology based techniques including scatterometry and reflectometry implementations and associated analysis algorithms are commonly used to characterize critical dimensions, film thicknesses, composition and other parameters of nanoscale structures.

Most advanced logic and memory devices fabricated at semiconductor device fabrication nodes below 20 nanometers are constructed using multiple patterning processes. Exemplary multiple patterning processes include self-aligned double patterning (SADP), self-aligned triple patterning (SATP), and self-aligned quadruple patterning (SAQP) techniques.

In one example, a SAQP fin formation process achieves a target pitch that is one-quarter of the pitch obtainable with conventional single pattern lithography. In one example, at least fourteen steps are required to generate the fin structures. These steps include lithography, etch, and strip steps that must be precisely controlled to realize the fin structures with the desired pitch and profile. The final pitch values and fin profile (e.g. CD, SWA) achieved by the SAQP fin formation process are impacted by structural parameter values from previous steps (e.g., resist profile parameters, spacer film thicknesses, and others).

Currently, measurements of overlay are predominantly performed using optical methods, based on either optical imaging or non-imaging diffraction (scatterometry). However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

As devices (e.g., logic and memory devices) move toward smaller nanometer-scale dimensions, characterization becomes more difficult. Devices incorporating complex three-dimensional geometry and materials with diverse physical properties contribute to characterization difficulty. For example, modern memory structures are often high-aspect ratio, three-dimensional structures that make it difficult for optical radiation to penetrate to the bottom layers. Optical metrology tools utilizing infrared to visible light can penetrate many layers of translucent materials, but longer wavelengths that provide good depth of penetration do not provide sufficient sensitivity to small anomalies. In addition, the increasing number of parameters required to characterize complex structures (e.g., FinFETs), leads to increasing parameter correlation. As a result, the parameters characterizing the target often cannot be reliably decoupled with available measurements. For some structural parameters, such as edge placement error (EPE), there is currently no high throughput (e.g., optical) measurement solution.

In another example, opaque, high-k materials are increasingly employed in modern semiconductor structures. Optical radiation is often unable to penetrate layers constructed of these materials. As a result, measurements with thin-film scatterometry tools such as ellipsometers or reflectometers are becoming increasingly challenging.

In some examples, optical overlay metrology is also employed, but optical overlay measurements require specialized metrology targets to characterize structures fabricated by multiple patterning techniques. In existing methods, overlay error is typically evaluated based on measurements of specialized target structures formed at various locations on the wafer by a lithography tool. The target structures may take many forms, such as a box in box structure. In this form, a box is created on one layer of the wafer and a second, smaller box is created on another layer. The localized overlay error is measured by comparing the alignment between the centers of the two boxes. Such measurements are taken at locations on the wafer where target structures are available.

Unfortunately, these specialized target structures often do not conform to the design rules of the particular semiconductor manufacturing process being employed to generate the electronic device. This leads to errors in estimation of overlay errors associated with actual device structures that are manufactured in accordance with the applicable design rules.

In one example, image-based optical overlay metrology is severely limited by the resolution of imaging at optical wavelengths. Thus, only targets with features much larger than the design rule can be measured. Image-based optical overlay metrology often requires the pattern to be resolved with an optical microscope that requires thick lines with critical dimensions far exceeding design rule critical dimensions.

In another example, scatterometry-based optical overlay metrology based on 0th order diffraction has very low sensitivity to small overlay errors as the sensitivity decreases with the pitch of the periodic targets. This drives the pitch to much larger dimensions than the design rule of the device. Moreover, the accuracy of this measurement approach degrades dramatically in the presence of any asymmetry in any of the layers where overlay is measured. In addition, this approach cannot differentiate between positive and negative overlay errors in a single measurement.

In another example, scatterometry-based optical overlay metrology based on diffraction orders higher than zero also require relatively large pitch targets to generate sufficient signal at nonzero propagating diffraction orders. In some examples, pitch values in the range 500-800 nm may be used. Meanwhile, actual device pitches for logic or memory applications (design rule dimensions) may be much smaller, e.g., in the range 100-400 nm, or even below 100 nm. In addition, the accuracy of this approach degrades dramatically in the presence of any asymmetry in any of the layers where overlay is measured.

Atomic force microscopes (AFM) and scanning-tunneling microscopes (STM) are able to achieve atomic resolution, but they can only probe the surface of the specimen. In addition, AFM and STM microscopes require long scanning times.

Scanning electron microscopes (SEM) achieve intermediate resolution levels, but are unable to penetrate structures to sufficient depth without destroying the sample. Thus, high-aspect ratio holes are not characterized well. In addition, the required charging of the specimen has an adverse effect on imaging performance.

Transmission electron microscopes (TEM) achieve high resolution levels and are able to probe arbitrary depths, but TEM requires destructive sectioning of the specimen.

In another example, an x-ray overlay measurement method is based on identifying the diffracted x-ray energy redistribution between the diffraction orders ("lobes") at a fixed (normal) incidence. This approach is described in U.S. Pat. No. 7,481,579 to Yokhim et al., and assigned to Jordan Valley Applied Radiation, Ltd. This quantity has a relatively low sensitivity to overlay and is strongly correlated to CD geometrical parameters because it does not consider the intensity distribution within each diffraction order. Thus, either an external metrology system or a computationally expensive simulation is required to calibrate out the effect of CD. Either of these approaches is limited in accuracy and precision due to the high correlation between CD parameters (e.g., asymmetry) and overlay.

In another example, an x-ray overlay measurement method is based on a modulation of the measured intensity signal as the wafer is rotated about an axis that lies in the plane of wafer surface. Further details are described in U.S. Patent Publication No. 2015/0117610 A1 by Veldman et al., the contents of which are incorporated herein by reference in their entirety. In this example, the measured periodicity is projected into the dimension normal to the wafer surface, but not into a direction parallel to the wafer surface and perpendicular to the periodic dimension.

In summary, semiconductor device yield at device fabrication nodes below 20 nanometers for logic devices and advanced DRAM, and vertical or planar NAND devices is a complex function of many parameters, including film thicknesses, profile parameters of patterned lines, overlay errors, and edge placement errors (EPE). Of these, EPE has the most demanding process window and requires metrology and control of CD and overlay. Currently there is no high-throughput, optical metrology solution for EPE measurements and many on-device overlay measurement applications. In addition, the absence of adequate metrology makes it challenging to define control schemes to improve device yield.

Future metrology applications present challenges for metrology due to increasingly small resolution requirements, multi-parameter correlation, increasingly complex geometric structures, and increasing use of opaque materials. Thus, methods and systems for improved overlay and shape measurements are desired.

SUMMARY

Methods and systems for performing overlay and edge placement errors of structures and materials based on x-ray diffraction measurement data are presented. In one aspect, x-ray diffraction measurements of a metrology target are performed at a number of different angles of incidence and azimuth angles as measured with reference to a coordinate frame fixed to the metrology target. The overlay error between different semiconductor layers of a metrology target is estimated based on the intensity variation within each x-ray diffraction order measured at multiple, different angles of incidence and multiple, different azimuth angles.

The vertical stacking of two or more structures in different layers of the metrology target affects the x-ray diffracted signal in a strong and unique way when measurements are made at multiple, different angles of incidence and multiple, different azimuth angles. Thus, the values of overlay and shape parameters are estimated based on the measured intensities.

In a further aspect, the estimation of overlay involves a parameterization of the intensity modulations of common orders such that a low frequency shape modulation is described by a set, or ratio, of basis functions and a high frequency overlay modulation is described by an affine-circular function that includes a parameter indicative of the overlay. By fitting measured intensity signals to phenomenological, simple functions, overlay offsets associated with multiple layers may be estimated in a computationally efficient manner. As a result, the measurements are performed at a relatively low computational cost and without external reference metrology, thus overcoming the limitations of current methods based on SEM, optical metrology, or other proposed x-ray metrology techniques.

In another aspect, a set of angles of incidence and azimuth angles are designed to enhance the spatial frequency of the overlay modulation such that sensitivity to overlay is increased and correlation between overlay and shape parameters is minimized.

In another aspect, an overlay target is provided that exhibits sensitivity to overlay in two different directions based on x-ray diffraction measurements of the metrology target performed at a number of different angles of incidence and azimuth angles. In some embodiments, the overlay metrology target includes any two layers of a 2D periodic structure with a set of equal grating numbers in one direction (e.g., the x-direction) and in an orthogonal direction (e.g., the y-direction). In some other embodiments, the overlay metrology target includes three or more layers. The first layer includes a 1D periodic structure.

In another aspect, the overlay metrology target is optimized specifically to increase the independence of overlay signals from each the constituent layers and maximize the precision and accuracy of the overlay measurements.

In some embodiments, a multiple layer overlay metrology target is designed such that the set of separation parameters between each combination of two layers is distinct and the minimum separation distance between all layer combinations is maximized subject to a constraint on the overall height of the metrology target.

In some embodiments, a multiple layer overlay metrology target is designed with different pitch at different layers such that a diffraction order arising from one layer constructively interferes with a different diffraction order of another layer.

In some embodiments, a multiple layer overlay metrology target is designed with different pitch orientations at different layers such that a diffraction order arising from one layer constructively interferes with a different diffraction order of another layer.

In another further aspect, a value of a shape parameter of any of the structures comprising the metrology target is estimated based on a fitting analysis of the detected intensities of the diffraction orders with a measurement model. In some examples, the estimation of overlay and the estimation of one or more shape parameter values are performed simultaneously.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Figure 1:
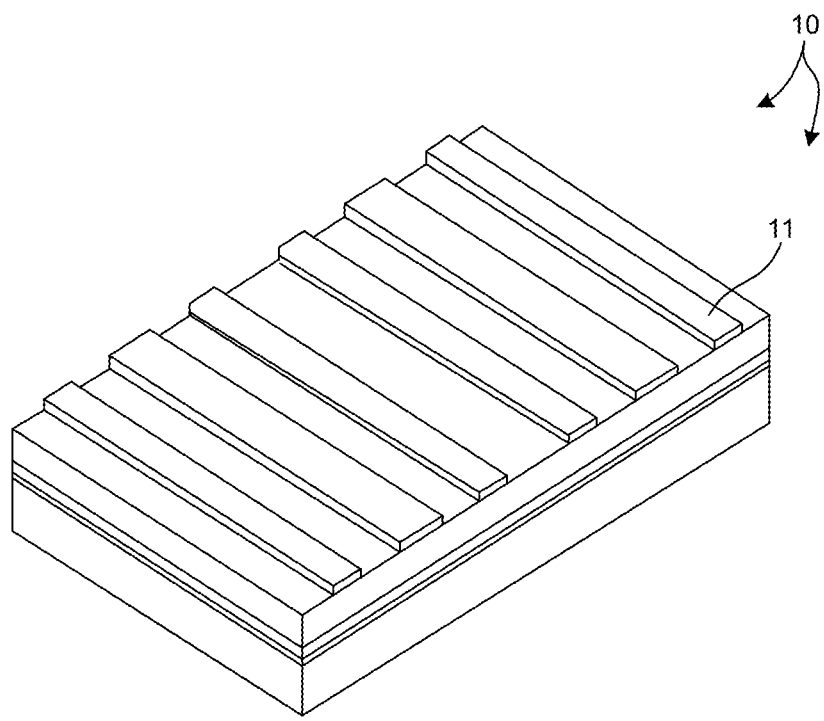
FIG. 1 is a diagram illustrative of a hardmask pattern of line structures 11 fabricated in a static random access memory (SRAM) area 10 of a microelectronic chip.
Figure 2:
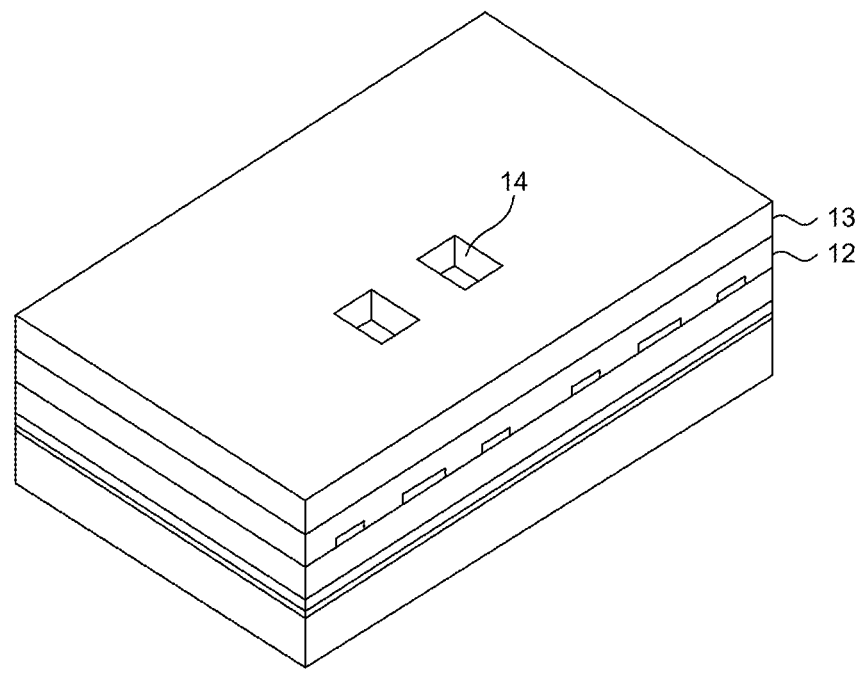
FIG. 2 is a diagram illustrative of a bottom anti-reflective coating (BARC) layer 12 and a resist layer 13 disposed on top of the pattern of line structures depicted in FIG. 1.

FIG. 1 depicts a hardmask pattern of line structures 11 fabricated in a static random access memory (SRAM) area 10 of a microelectronic chip. The complex layout of the active region is created by combining multiple patterning techniques with cut masks. Cut masks selectively remove portions of the hardmask layer that is used to pattern the substrate into active regions. FIG. 2 depicts a bottom anti-reflective coating (BARC) layer 12 and a resist layer 13 disposed on top of the pattern of line structures depicted in FIG. 1. The resist layer is used to selectively remove part of the hardmask pattern below the openings 14 of the resist layer 13. As depicted in FIG. 1, the hardmask pattern of line structures 11 is buried by the BARC layer 12, even within the openings 14 of the resist layer 13.

To provide adequate yield for the cut mask process, reliable measurements for shape parameters (e.g., CD, HT, SWA), film thicknesses, and overlay are required. A calculation of overlay reveals that it is a function of many structural parameters from previous steps of a quadruple patterning process. The distribution of the gap between the edge of the cut and the adjacent line structure, and hence the yield of the process, depends on a complex interaction of all the process parameters.

In another example, edge placement distance (EPD) and the associated edge placement error (EPE) is an important parameter to monitor and control after device electrical contacts are made. The difference between the desired and the actual EPD is called EPE. EPD and EPE are a function of both overlay and CD errors.

Methods and systems for performing overlay and edge placement errors of structures and materials based on x-ray diffraction measurement data are presented. In some embodiments, overlay and shape parameter (e.g., CD) measurements of design rule targets are performed simultaneously. The methods and systems presented herein may be applied to two and three dimensional design rule metrology targets, located within or outside of functional die. The measurement methods and systems described herein are applicable to the 2x, 1x, and 0x technology nodes, and beyond. In addition to providing overlay metrology capability, the methods and systems described herein enhance the precision and accuracy of shape parameter measurements by strongly de-correlating geometric parameters of the measured structures.

The use of high brightness x-ray radiation enables high flux x-ray radiation penetration into opaque areas of the target. In some examples, small-angle x-ray scatterometry (SAXS) measurements are employed in either grazing incidence or transmission incidence configurations. A SAXS measurement involves illuminating a sample with an X-ray beam and detecting the intensities of the resulting diffraction orders for multiple angles of incidence relative to the sample, multiple wavelengths, or both. Examples of measureable geometric parameters using SAXS includes pore size, pore density, line edge roughness, line width roughness, side wall angle, profile, critical dimension, overlay, edge placement error, and pitch. Examples of measureable material parameters include electron density, elemental identification and composition. In some examples, SAXS enables the measurement of features smaller than 10 nm as well as advanced semiconductor structures such as spin-transfer-torque MRAM where measurements of geometrical parameters and material parameters are needed.

Figure 3:
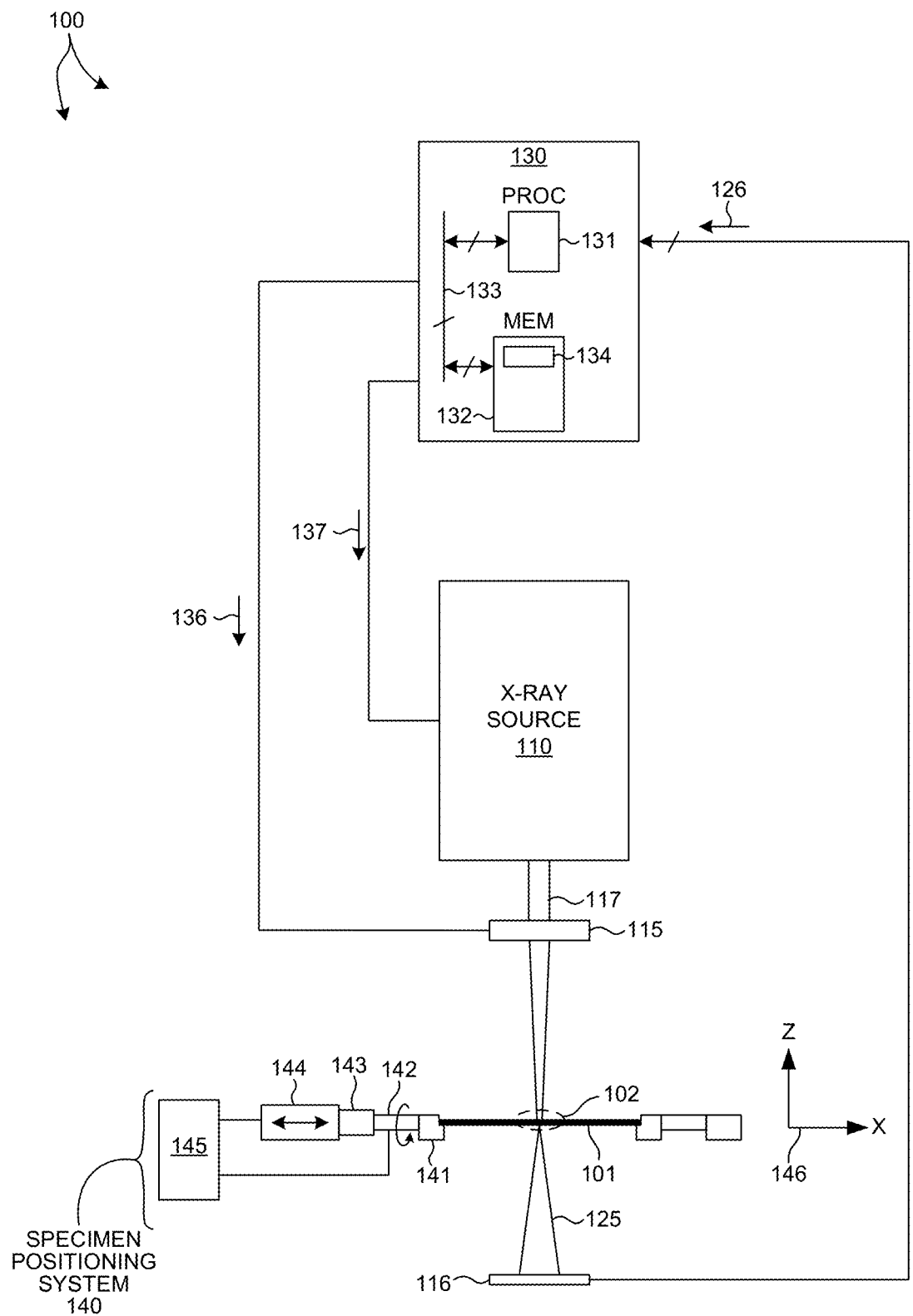
FIG. 3 is a diagram illustrative of an embodiment of an x-ray metrology tool 100 for measuring characteristics of a specimen in accordance with the exemplary methods presented herein.

FIG. 3 illustrates an embodiment of a metrology tool 100 for measuring characteristics of a specimen in accordance with the exemplary methods presented herein. As shown in FIG. 3, the system 100 may be used to perform transmission SAXS measurements over an inspection area 102 of a specimen 101 disposed on a specimen positioning system 140. In some embodiments, the inspection area 102 has a spot size of fifty micrometers or less.

In the depicted embodiment, metrology tool 100 includes an x-ray illumination source 110 configured to generate x-ray radiation suitable for SAXS measurements. In some embodiments, the x-ray illumination system 110 is configured to generate wavelengths between 0.01 nanometers and 1 nanometer. X-ray illumination source 110 produces an x-ray beam 117 incident on inspection area 102 of specimen 101.

In general, any suitable high-brightness x-ray illumination source capable of generating high brightness x-rays at flux levels sufficient to enable high-throughput, inline metrology may be contemplated to supply x-ray illumination for SAXS measurements. In some embodiments, an x-ray source includes a tunable monochromator that enables the x-ray source to deliver x-ray radiation at different, selectable wavelengths.

In some embodiments, one or more x-ray sources emitting radiation with photon energy greater than 15 keV are employed. By way of non-limiting example, any of a particle accelerator source, a liquid anode source, a rotating anode source, a microfocus source, a microfocus rotating anode source, and an inverse Compton source may be employed as x-ray source 110. In one example, an inverse Compton source available from Lyncean Technologies, Inc., Palo Alto, Calif. (USA) may be contemplated. Inverse Compton sources have an additional advantage of being able to produce x-rays over a range of photon energies, thereby enabling the x-ray source to deliver x-ray radiation at different, selectable wavelengths.

Figure 4:
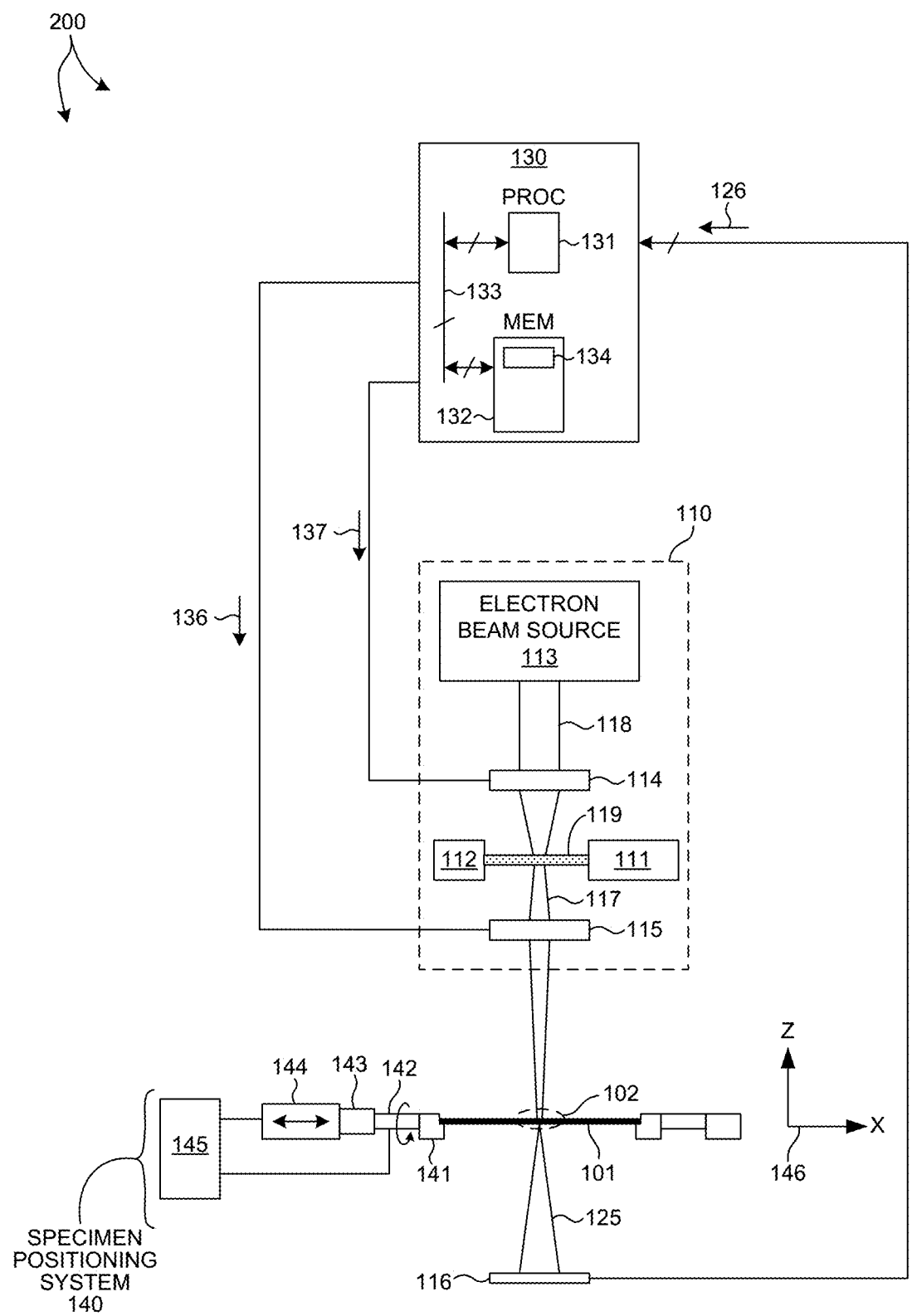
FIG. 4 is a diagram illustrative of another embodiment of an x-ray metrology tool 200 for measuring characteristics of a specimen in accordance with the exemplary methods presented herein.

Exemplary x-ray sources include electron beam sources configured to bombard solid or liquid targets to stimulate x-ray radiation. FIG. 4 depicts a metrology tool 200 for measuring characteristics of a specimen in accordance with the exemplary methods presented herein. Like numbered elements of metrology tool 100 and 200 are analogous. However, in the embodiment depicted in FIG. 4, x-ray illumination source 110 is a liquid metal based x-ray illumination system. A jet of liquid metal 119 is produced from a liquid metal container 111 and collected in a liquid metal collector 112. A liquid metal circulation system (not shown) returns liquid metal collected by collector 112 to liquid metal container 111. The jet of liquid metal 119 includes one or more elements. By way of non-limiting example, the jet of liquid metal 119 includes any of Aluminum, Gallium, Indium, Tin, Thallium, and Bismuth. In this manner, the jet of liquid metal 119 produces x-ray lines corresponding with its constituent elements. In one embodiment, the jet of liquid metal includes a Gallium and Indium alloy. In some embodiments, the x-ray illumination system 110 is configured to generate wavelengths between 0.01 nanometers and 1 nanometer. An electron beam source 113 (e.g., electron gun) produces a stream of electrons 118 that is directed by electron optics 114 to the jet of liquid metal 119. Suitable electron optics 114 includes electromagnets, permanent magnets, or a combination of electromagnets and permanent magnets for focusing the electron beam and directing the beam at the liquid metal jet. The coincidence of the jet of liquid metal 119 and the stream of electrons 118 produces an x-ray beam 117 incident on inspection area 102 of specimen 101.

In one embodiment, the incident x-ray beam 117 is at the Indium kα line of 24.2 keV. The x-ray beam is collimated down to less than one milliradian divergence using multilayer x-ray optics for transmission SAXS measurements.

Methods and systems for generating high brightness, liquid metal x-ray illumination are described in U.S. Pat. No. 7,929,667, issued on Apr. 19, 2011, to KLA-Tencor Corp., the entirety of which is incorporated herein by reference.

As depicted in FIG. 3, x-ray optics 115 shape and direct incident x-ray beam 117 to specimen 101. In some examples, x-ray optics 115 includes an x-ray monochromator to monochromatize the x-ray beam that is incident on the specimen 101. In one example, a crystal monochromator such as a Loxley-Tanner-Bowen monochromator is employed to monochromatize the beam of x-ray radiation. In some examples, x-ray optics 115 collimate or focus the x-ray beam 117 onto inspection area 102 of specimen 101 to less than 1 milliradian divergence using multilayer x-ray optics. In some embodiments, x-ray optics 115 includes one or more x-ray collimating mirrors, x-ray apertures, x-ray beam stops, refractive x-ray optics, diffractive optics such as zone plates, specular x-ray optics such as grazing incidence ellipsoidal mirrors, polycapillary optics such as hollow capillary x-ray waveguides, multilayer optics, or systems, or any combination thereof.

X-ray detector 116 collects x-ray radiation 125 scattered from specimen 101 and generates an output signal 126 indicative of properties of specimen 101 that are sensitive to the incident x-ray radiation in accordance with a SAXS measurement modality. In some embodiments, scattered x-rays 125 are collected by x-ray detector 116 while specimen positioning system 140 locates and orients specimen 101 to produce angularly resolved scattered x-rays. In some embodiments, the x-ray detector 116 is able to resolve one or more x-ray photon energies and produces signals for each x-ray energy component indicative of properties of the specimen. In some embodiments, the x-ray detector 116 includes any of a CCD array, a microchannel plate, a photodiode array, a microstrip proportional counter, a gas filled proportional counter, a scintillator, or a fluorescent material. In some embodiments, the x-ray detector 116 includes a single photon counting detector that detects the position and number of detected photons.

In some embodiments, x-ray detector 116 is maintained in the same atmospheric environment as specimen 101 (e.g., gas purge environment). However, in some embodiments, the distance between specimen 101 and x-ray detector 116 is lengthy (e.g., greater than one meter). In these embodiments, environmental disturbances (e.g., air turbulence) contribute noise to the detected signals. Hence in some embodiments, one or more of the x-ray detectors is maintained in a localized, vacuum environment separated from the specimen (e.g., specimen 101) by a vacuum window.

Figure 6:
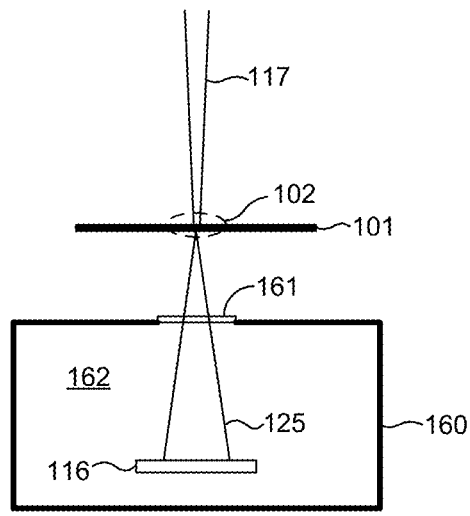
FIG. 6 is a diagram illustrative of a x-ray detector 116 of metrology systems 100, 200, and 300 contained in a vacuum environment 162 separate from specimen 101.

FIG. 6 is a diagram illustrative of a vacuum chamber 160 containing x-ray detector 116 in one embodiment. In a preferred embodiment, vacuum chamber 160 includes a substantial portion of the path between specimen 101 and x-ray detector 116. An opening of vacuum chamber 160 is covered by vacuum window 161. Vacuum window 161 may be constructed of any suitable material that is substantially transparent to x-ray radiation (e.g., Beryllium). Scattered x-ray radiation 125 passes through vacuum window 161, enters vacuum chamber 160 and is incident on x-ray detector 116. A suitable vacuum environment 162 is maintained within vacuum chamber 160 to minimize disturbances to scattered x-ray radiation 125.

Figure 5:
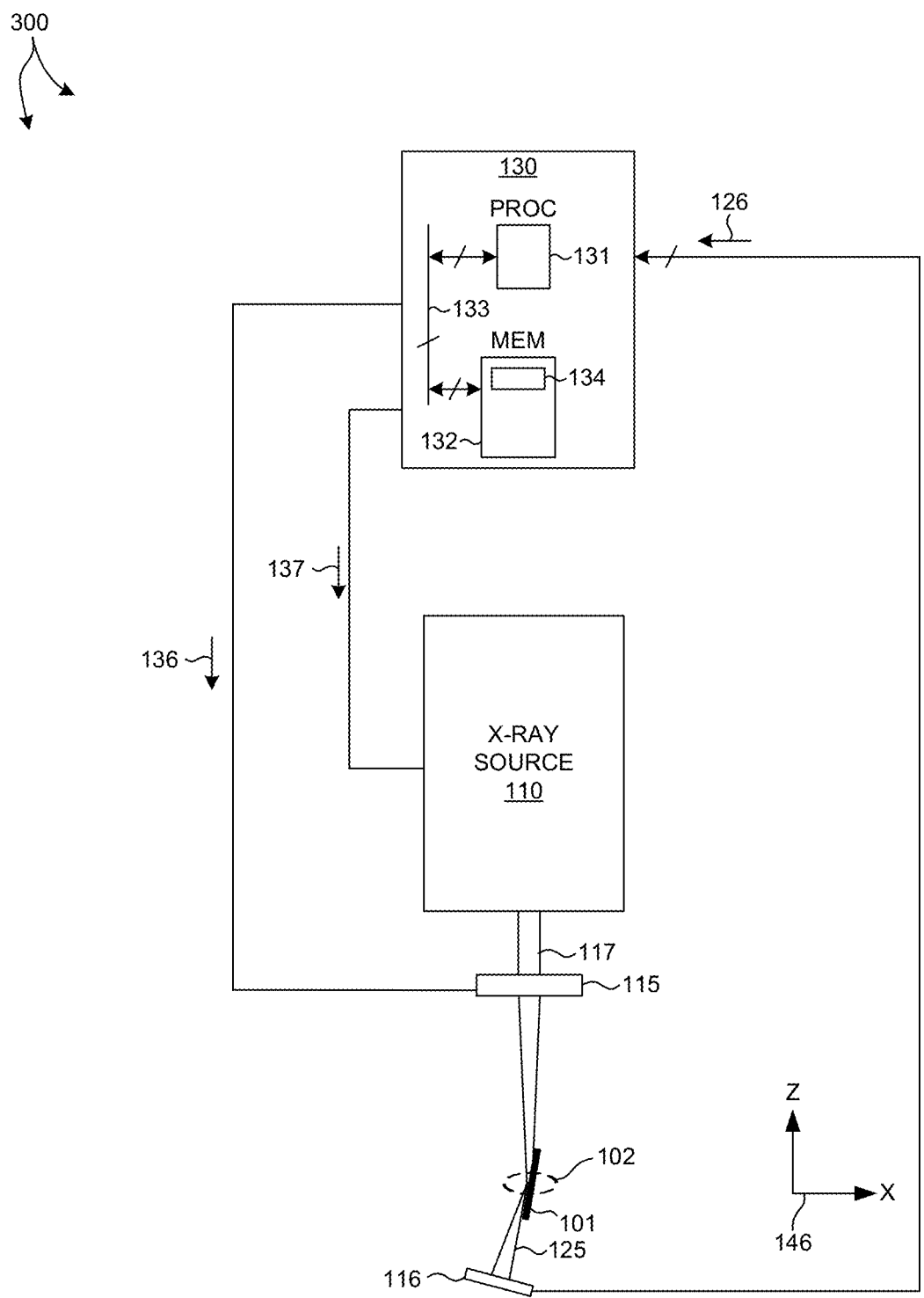
FIG. 5 is a diagram illustrative of yet another embodiment of an x-ray metrology tool 300 for measuring characteristics of a specimen in a grazing incidence mode in accordance with the exemplary methods presented herein.

FIG. 5 illustrates an x-ray metrology system 300 for performing semiconductor metrology measurements in accordance with the methods described herein. As illustrated in FIG. 5, x-ray metrology system 300 includes similar, like numbered elements described with reference to FIGS. 3 and 4. However, x-ray metrology system 300 operates in a grazing incidence mode. More specifically, x-ray metrology system 300 is configured as a grazing incidence small-angle x-ray scattering (GISAXS) measurement system. Typical angles of incidence and collection are approximately one degree as measured from the surface of the specimen, or approximately eighty nine degrees from an axis normal to the surface of the specimen. X-ray metrology system 300 is configured such that x-rays scattered from the specimen are collected by a detector while a sample handler (not shown) positions the specimen. In addition, any other particles produced during the interaction such as photoelectrons, x-rays produced through fluorescence, or ions can be detected. Metrology systems configured to perform GISAXS measurements require a high brightness x-ray source to maintain sufficient brightness over the relatively large sample area illuminated at small angles. For this reason, a liquid metal jet x-ray source 110 described with reference to FIG. 4 is particularly well suited for GISAXS measurements.

By way of non-limiting example, the x-ray metrology systems 100 and 200 illustrated in FIGS. 3 and 4, respectively, are configured as transmission small angle x-ray scatterometers (TSAXS) and the x-ray metrology system 300 illustrated in FIG. 5 is configured as a grazing incidence small angle x-ray scatterometer (GISAXS). However, in general, an x-ray metrology system configured to perform diffraction based overlay measurements and shape parameter measurements as described herein may employ any one or more of the following metrology techniques: transmission small angle x-ray scattering (TSAXS), grazing incidence small angle x-ray scattering (GISAXS), wide angle x-ray scattering (WAXS), x-ray diffraction (XRD), grazing incidence x-ray diffraction (GIXRD), and high resolution x-ray diffraction (HRXRD).

Metrology tool 100 also includes a computing system 130 employed to acquire signals 126 generated by SAXS detector 116 and determine properties of the specimen based at least in part on the acquired signals. As illustrated in FIG. 3, computing system 130 is communicatively coupled to SAXS detector 116.

In a further embodiment, computing system 130 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference in its entirety. Additional details regarding x-ray based measurements of semiconductor structures are provided in U.S. Patent Publication No. 2013/0304424 and U.S. Patent Publication No. 2015/0110249, which are incorporated herein by reference in their entireties.

In one further aspect, metrology tool 100 includes a computing system (e.g., computing system 130) configured to implement beam control functionality as described herein. In the embodiment depicted in FIG. 3, computing system 130 is configured as a beam controller operable to control any of the illumination properties such as intensity, divergence, spot size, polarization, spectrum, and positioning of the incident SAXS illumination beam 117.

As illustrated in FIG. 3, computing system 130 is communicatively coupled to SAXS detector 116. Computing system 130 is configured to receive measurement data 126 from SAXS detector 116. In one example, measurement data 126 includes an indication of the measured SAXS response of the specimen (i.e., intensities of the diffraction orders). Based on the distribution of the measured SAXS response on the surface of detector 116, the location and area of incidence of SAXS illumination beam 117 on specimen 101 is determined by computing system 130. In one example, pattern recognition techniques are applied by computing system 130 to determine the location and area of incidence of SAXS illumination beam 117 on specimen 101 based on measurement data 126. In some examples, computing system 130 communicates command signal 137 to illumination optics 115 to select the desired illumination wavelength and redirect and reshape SAXS illumination beam 117 such that incident SAXS illumination beam 117 arrives at the desired location and angular orientation with respect to specimen 101. In some other examples, computing system 130 communicates a command signal to wafer positioning system 140 to position and orient specimen 101 such that incident SAXS illumination beam 117 arrives at the desired location and angular orientation with respect to specimen 101. In some other examples, computing system 130 communicates a command signal 137 to x-ray source 110 to select the desired illumination wavelength and redirect and reshape SAXS illumination beam 117 such that incident SAXS illumination beam 117 arrives at the desired location and angular orientation with respect to specimen 101.

Figure 7:
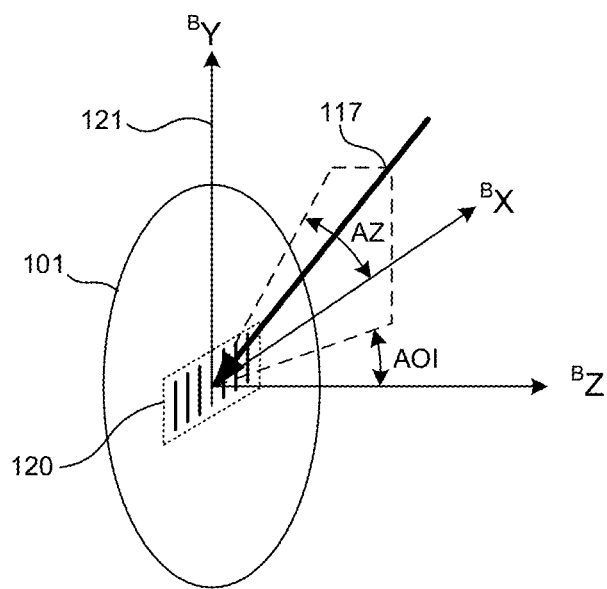
FIG. 7 is a diagram illustrative of a wafer 101 including a metrology target 120 illuminated by a beam of x-ray radiation at an angle of incidence and azimuth angle.

In one aspect, x-ray diffraction measurements of a metrology target are performed at a number of different angles of incidence and azimuth angles. FIG. 7 depicts wafer 101 including a metrology target 120. An x-ray illumination source illuminates metrology target 120 with a beam of x-ray radiation 117 at an angle of incidence, AOI, and an azimuth angle, Az. The angle of incidence and the azimuth angle of the beam of incident x-ray radiation are defined with respect to a coordinate frame $\{^BX, ^BY, ^BZ\}$ fixed to specimen 101. As depicted in FIG. 7, metrology target 120 includes a grating structure that extends in the $^BY$ direction and is periodic in the $^BX$ direction. The angle of incidence is defined as the angle of the projection of the incident beam onto the $^BX$-$^BZ$ plane with respect to the $^BZ$ axis. In this sense, changes in the angle of incidence can be viewed as a rotation of wafer 101 about the $^BY$ axis, in-plane with wafer 101. Similarly, the azimuth angle is defined as the angle of the projection of the incident beam onto the $^BX$-$^BY$ plane with respect to the $^BX$ axis. In this sense, changes in the azimuth angle can be viewed as a rotation of wafer 101 about the $^BZ$ axis, normal to wafer 101.

As illustrated in FIG. 3, metrology tool 100 includes a specimen positioning system 140 configured to both align specimen 101 and orient specimen 101 over a large range of out of plane angular orientations with respect the SAXS scatterometer. In other words, specimen positioning system 140 is configured to rotate specimen 101 over a large angular range about one or more axes of rotation aligned in-plane and normal to the surface of specimen 101. In some embodiments, specimen positioning system 140 is configured to rotate specimen 101 within a range of at least 90 degrees about one or more axes of rotation aligned in-plane and normal to the surface of specimen 101. In this manner, angle resolved measurements of specimen 101 are collected by metrology system 100 over any number of locations on the surface of specimen 101. In one example, computing system 130 communicates command signals to motion controller 145 of specimen positioning system 140 that indicate the desired position of specimen 101. In response, motion controller 145 generates command signals to the various actuators of specimen positioning system 140 to achieve the desired positioning of specimen 101.

By way of non-limiting example, as illustrated in FIG. 3, specimen positioning system 140 includes an edge grip chuck 141 to fixedly attach specimen 101 to specimen positioning system 140. A rotational actuator 142 is configured to rotate edge grip chuck 141 and the attached specimen 101 with respect to a perimeter frame 143. In the depicted embodiment, rotational actuator 142 is configured to rotate specimen 101 about the x-axis of the coordinate system 146 illustrated in FIG. 3. As depicted in FIG. 3, a rotation of specimen 101 about the z-axis is a rotation about the surface normal of specimen 101. Rotations about the x-axis and the y-axis (not shown) are out of plane rotations of specimen 101 that effectively tilt the surface of the specimen with respect to the metrology elements of metrology system 100. Although it is not illustrated, a second rotational actuator is configured to rotate specimen 101 about the y-axis. A linear actuator 144 is configured to translate perimeter frame 143 in the x-direction. Another linear actuator (not shown) is configured to translate perimeter frame 143 in the y-direction. In this manner, every location on the surface of specimen 101 is available for measurement over a range of rotations about the axes of coordinate frame $\{^{B}X, ^{B}Y, ^{B}Z\}$ fixed to specimen 101.

In general, specimen positioning system 140 may include any suitable combination of mechanical elements to achieve the desired linear and angular positioning performance, including, but not limited to goniometer stages, hexapod stages, angular stages, and linear stages.

In the embodiments depicted in FIGS. 3-5, a single beam of incident x-ray radiation is illustrated. The orientation of the single beam with respect to the wafer is defined by a single angle of incidence and azimuth angle. For embodiments employing a single illumination beam, x-ray diffraction measurements associated multiple, different angles of incidence and azimuth angles are performed sequentially. However, in general, x-ray diffraction measurements associated with multiple, different angles of incidence and azimuth angles may be performed simultaneously. In some embodiments, one or more x-ray sources and one or more sets of x-ray optics may be employed such that the metrology target is illuminated simultaneously from multiple directions, either discrete or continuous in angle of incidence and azimuth angle.

As described hereinbefore, x-ray diffraction measurements of a metrology target are performed at a number of different angles of incidence and azimuth angles. In a further aspect, the overlay error between different semiconductor layers of a metrology target is estimated based on the intensity variation within each x-ray diffraction order measured at multiple, different angles of incidence and multiple, different azimuth angles.

The vertical stacking of two or more structures in different layers of the metrology target affects the x-ray diffracted signal in a strong and unique way when measurements are made at multiple, different angles of incidence and multiple, different azimuth angles. Thus, the values of overlay and shape parameters may be estimated based on the measured intensities.

In a further aspect, the estimation of overlay involves a parameterization of the intensity modulations of common orders such that a low frequency shape modulation is described by a set, or ratio, of basis functions and a high frequency overlay modulation is described by an affine-circular function that includes a parameter indicative of the overlay.

Figure 8:
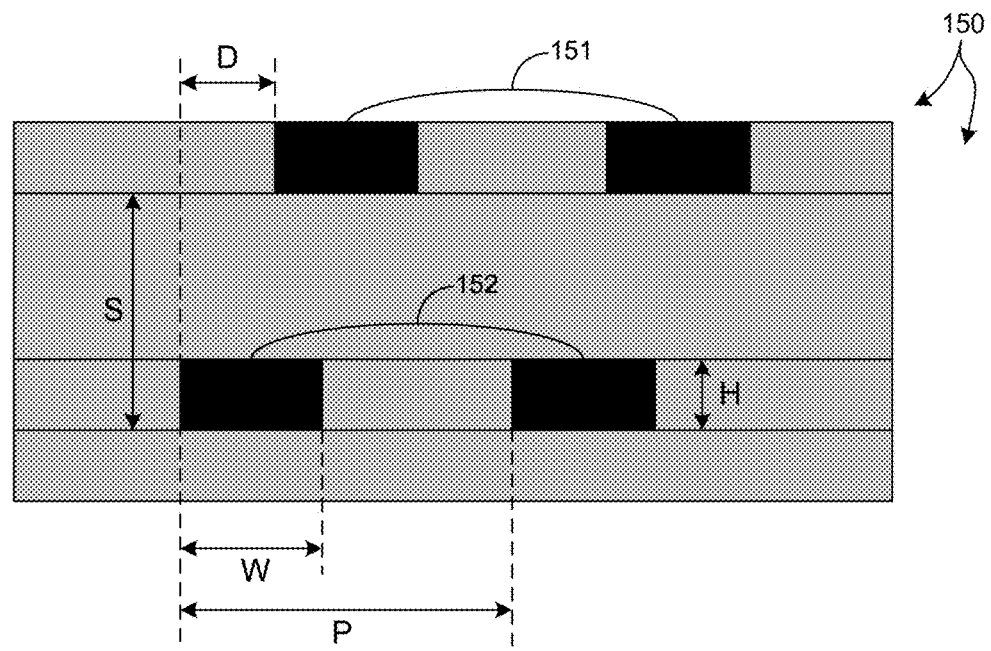
FIG. 8 depicts a layered metrology target 150 including two periodic arrays of lines 151 and 152 in different layers.

In one example, the parameterization is derived from an analysis of a canonical overlay problem. FIG. 8 depicts a layered metrology target 150 including two periodic arrays of lines 151 and 152, each having periodicity, P. The arrays of lines are separated vertically by a distance, S, and the arrays of lines are offset by overlay distance, D. The height and width of each of the arrays of lines are given by the parameters H and W, respectively.

In addition, the electron density of the top line is given by the parameter, $\delta 0$, and the bottom line by $\delta 1$. The metrology target 150 is illuminated by a beam of x-ray radiation having a wavelength, $\lambda$. The beam of incident x-ray radiation impinges on the metrology target at an angle of incidence, $\theta$, and an azimuth angle, $\varphi$, where $\varphi=0$ when the projection of the light ray is perpendicular to the periodicity of the grating. For such a grating we define the wavelength number as $k_0=2\pi/\lambda$, and the grating number in the 1D periodic direction as $k_x=2\pi/P$, where m is the order number. The angle of incidence is measured from the axis normal to the wafer.

An analysis of the diffraction intensity provides an approximation of the intensity of each order as illustrated in equation (1).

$$I = \left(\frac{k_0 WH}{P\cos\theta}\right)^2 \text{sinc}\left(\frac{mk_x W}{2}\right)^2 \text{sinc}\left(\frac{mk_x H \tan\theta\cos\varphi}{2}\right)^2 \qquad (1)$$
$$(\delta_0^2 + \delta_1^2 + 2\delta_0\delta_1\cos(mk_x(D + S \tan\theta\cos\varphi)))$$

Equation (1) illustrates that not only is there a modulation of the order intensity by changing the angle of incidence, $\theta$, but also by changing the azimuth angle, $\varphi$. Stated another way, we can expect a modulation of the diffraction orders from the projection of the grating periodic dimension aligned with $^{B}X$ into the direction aligned with $^{B}Z$ by changing the angle of incidence. In addition, we can expect a modulation of the diffraction orders from the projection of the grating periodic dimension aligned with $^{B}X$ into the direction aligned with $^{B}Y$ by changing the azimuth angle. In addition, changes in angle of incidence and azimuth angle can be coordinated to accentuate the overlay signal. For example, changing the azimuth angle can slow the shape and overlay modulation due to changes in angle of incidence by the scaling factor, $\cos(\varphi)$. Finally, equation (1) also illustrates that the modulation of the order intensity due to shape parameters W and H are typically of low spatial frequency relative to the overlay modulation described by the last term of equation (1).

Due to the relatively low spatial frequency modulation due to shape, this modulation can be modeled by a low order polynomial, e.g., a linear or quadratic function. The modulation due to separation distance, S, and overlay, D, can then be represented by the cosine term illustrated in equation (1). Hence, a simplified model of the intensity for each order takes an additive or multiplicative form as illustrated by equations (2a) and (2b), respectively.

$$I = \sum_{j=0}^{N} a_j\theta^j + b\cos(mk_x(D + S \tan\theta\cos\varphi)) \qquad (2a)$$

-continued $$I = \left(\sum_{j=0}^{N} a_j \theta^j\right)(b\cos(mk_x(D + S \tan\theta\cos\varphi))) \quad (2b)$$

The shape function defined by the first term of equation (2a) and the first factor of equation (2b) model the shape modulation as a linear combination of basis functions, $\theta j$, weighted by parameters $aj$, without explicit knowledge of the shape. As illustrated in equations (2a) and (2b), a monomial basis is employed to describe the shape change. However, in general, any polynomial, rational, or basis set of any kind may be employed.

The parameter, b, defines the modulation depth. Parameters D and S define the overlay. By changing the angle of incidence, azimuth angle, or both, the resulting data for any order may be fit to the parameters $a_j$, b, D, and S using any suitable curve fitting routine. The overlay is given by the fit for the parameter, D.

The simplified model for overlay measurement described hereinbefore is illustrative of a phenomenological approach to modeling the intensity variations of diffraction orders based on changes in angle of incidence and azimuth angle. In general, the model can be based on other waveforms and non-polynomial basis functions.

By fitting measured intensity signals to phenomenological, simple functions, overlay offsets associated with multiple layers may be estimated in a computationally efficient manner. As a result, the measurements are performed at a relatively low computational cost and without external reference metrology, thus overcoming the limitations of current methods based on SEM, optical metrology, or other proposed x-ray metrology techniques.

Figure 9:
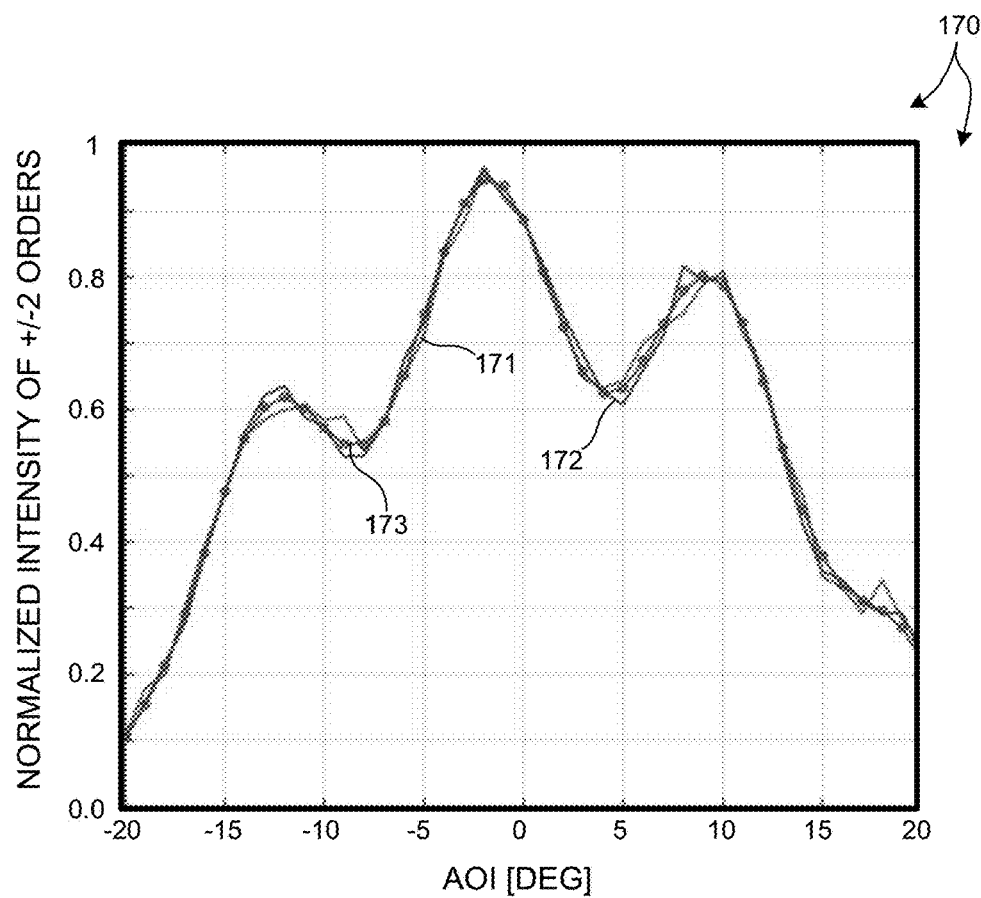
FIG. 9 depicts a plot 170 indicative of a simulation of a fitting of a simplified model of intensity and corresponding measured values of the −2 and +2 diffraction orders for a range of angles of incidence for the metrology target illustrated in FIG. 8.

FIG. 9 depicts a plot 170 indicative of simulation of the fitting results for the metrology target 150 depicted in FIG. 8. Plotline 171 depicts a simulation of the normalized intensity of the −2 diffraction order for a range of angles of incidence. Plotline 172 depicts a simulation of the normalized intensity of the +2 diffraction order for the same range of angles of incidence. Plotline 173 depicts the results of a fitting of the simulated diffraction intensities by a model of type described with reference to equation (2). As illustrated in FIG. 9, the simplified model described with reference to equation (2) provides a close fit to the simulated intensity values.

As illustrated by equation (2), the overlay modulation is an even function in the diffraction order. Thus, data from both positive and negative orders may be averaged, or fit jointly. In addition, multiple orders may be fit jointly. In some examples, different ranges in angle space may be employed for each different diffraction order.

In the embodiment depicted in FIG. 1, computing system 130 is configured as model building and analysis engine 180 and is operable to implement model building and analysis functionality as described herein.

Figure 11:
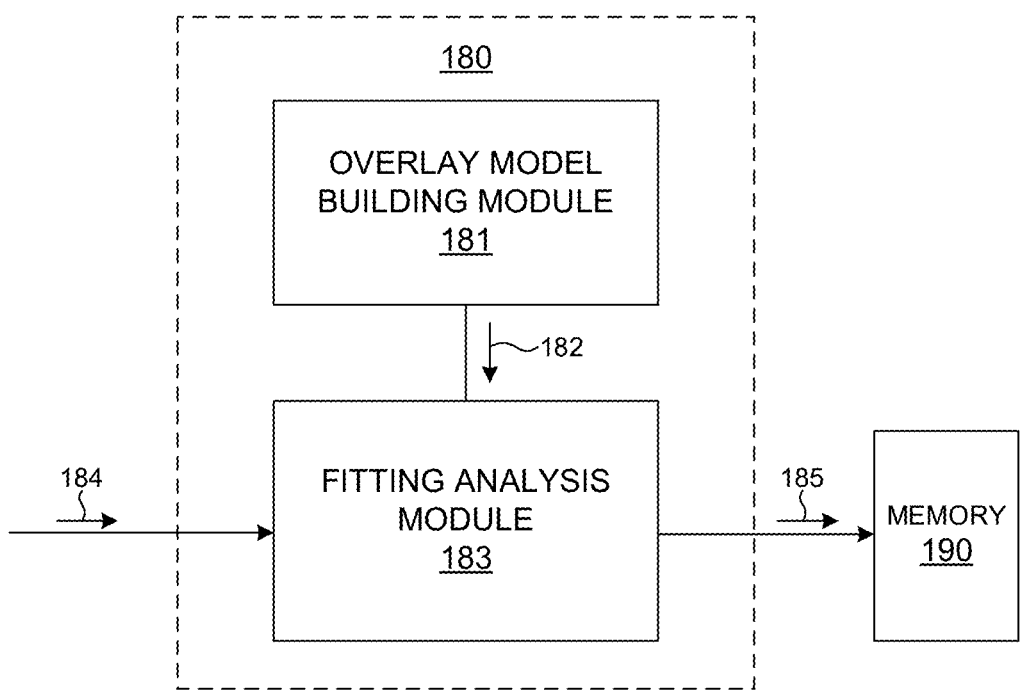
FIG. 11 is a diagram illustrative of a model building and analysis engine 180 configured to estimate overlay based on modulations of intensity measurement data as described herein.

FIG. 11 is a diagram illustrative of model building and analysis engine 180 configured to estimate overlay based on modulations of intensity measurement data as described herein. As depicted in FIG. 11, model building and analysis engine 180 includes an overlay model building module 181 that generates a simplified model 122 for overlay measurement such as the model described with reference to equation (2a) or (2b). Model 122 captures the intensity variations of various diffraction orders based on changes in angle of incidence and azimuth angle.

Fitting analysis module 183 receives the measurement signals 126 indicative of the measured intensities of the diffraction orders and estimates the overlay of the measured overlay metrology target based on the measured data. In some examples, the fitting analysis is an iterative optimization that involves minimizing differences between the measured intensities of the diffraction orders and calculated intensities.

After convergence of the iterative optimization, the estimated overlay value(s) of the measured overlay metrology target 185 is stored in a memory 190.

In a further aspect, a set of angles of incidence and azimuth angles are designed to enhance the spatial frequency of the overlay modulation such that sensitivity to overlay is increased and correlation between overlay and shape parameters is minimized. In some examples, the intensity signals are collected and analyzed at a limited number of angles of incidence and azimuth angles.

In some embodiments, a recursive optimization of a physical model of the x-ray diffraction measurement is employed to arrive at a set of angles of incidence and azimuth angles that achieves a maximum sensitivity to overlay and minimizes the correlation between overlay and shape parameters.

In another further aspect, an overlay target is provided that exhibits sensitivity to overlay in two different directions based on x-ray diffraction measurements of the metrology target performed at a number of different angles of incidence and azimuth angles. For a simple orthogonal 2D periodic structure, equation (2) can be extended to include two independent modulation factors as illustrated in equation (3).

$$I=M(\theta,\varphi)+(1+b\;\cos(mk_x(D_x+S\tan\theta\cos\varphi))\cos(mk_y(D_y+S\tan\theta\sin\varphi))) \quad (3a)$$

$$I=M(\theta,\varphi)*(1+b\;\cos(mk_x(D_x+S\tan\theta\cos\varphi))\cos(mk_y(D_y+S\tan\theta\sin\varphi))) \quad (3b)$$

In some embodiments, the overlay metrology target includes any two layers of a 2D periodic structure with a set of equal grating numbers in one direction (e.g., the x-direction) and in an orthogonal direction (e.g., the y-direction).

In some other embodiments, the overlay metrology target includes three layers. The first layer includes a 1D periodic structure. The second layer includes another 1D periodic structure oriented at an angle (e.g., orthogonal) with respect to the 1D periodic structure located in the first layer. The third layer includes a 2D periodic structure (e.g., an array of posts). The periodicity of the 2D grating has wave vectors that coincide with the 1D periodic structures located below it. In this manner, the overlay associated with the two different directions (e.g., x and y directions) is estimated independently. For example, in one direction, the orders with grating numbers in common between the first and third layers are analyzed as if they were modulated with a single modulation factor. For the other direction, the orders with grating numbers in common between the second and third layers are analyzed as if they were modulated with another modulation factor. In another example, the overlays could be estimated jointly as both modulation factors include the parameter, S. In another example, both overlay values can be estimated by a single change in angle of incidence when crossed gratings are employed in the first and second layers, provided that the azimuth angle is neither zero nor ninety degrees.

In some other embodiments, the overlay metrology target includes four layers including two sets of 1D periodic gratings from which the overlay in both directions is measured.

In general, there is no theoretical limit to the number of layers and overlay parameters that can be estimated based on x-ray diffraction measurements performed at multiple, different angles of incidence and azimuth angles. The interference modulation illustrated in equations (2) and (3) indicates that when there is uniqueness in the separation parameter, S, between any two layers, the intensity signal as a function of AOI, Az, or both, will be independent and the overlay parameter is measureable. Thus, it is desirable to design a multiple layer overlay metrology target such that the set of separation parameters between each combination of two layers is distinct. However, in practice, as the number of layers grows, so does the number of combinations of layers taken two at a time. As a result, it becomes a challenge to design a metrology target having a unique or nearly unique set of separation distances between each of the combinations of two layers.

In some embodiments, the overlay metrology target is optimized specifically to increase the independence of overlay signals from each the constituent layers and maximize the precision and accuracy of the overlay measurements.

In some embodiments, a multiple layer overlay metrology target is designed such that the set of separation parameters between each combination of two layers is distinct and the minimum separation distance between all layer combinations is maximized subject to a constraint on the overall height of the metrology target.

In some embodiments, a multiple layer overlay metrology target is designed with different pitch at different layers such that a diffraction order arising from one layer constructively interferes with a different diffraction order of another layer. In one embodiment, a periodic grating structure located in a first layer has a pitch equal to 2A, where A is an arbitrary, positive valued constant. Another periodic structure located in a different layer has a pitch equal to 3A. In this example, the second diffraction order of the first layer constructively interferes with the third diffraction order of the second layer. Thus, the intensity measurements detected at these order pairs are dominated by overlay between the two layers. Conversely, intensity measurements detected at different order number pairs not subject to constructive interference in overlay are dominated by shape parameters. Thus, in some embodiments, a metrology overlay target is designed with specific grating structures to increase sensitivity to overlay at specific grating order pairs, and also provide intensity data useful for estimation of shape parameter values.

Similarly, a multiple layer overlay metrology target is designed with different pitch orientations at different layers such that a diffraction order arising from one layer constructively interferes with a different diffraction order of another layer. In general, a set of layers having different periodicities (e.g., different grating pitches), different pitch orientations, or any combination thereof, gives rise to a set of scattering vectors, each associated with a different layer. The overlay metrology target is designed such that a predetermined subset of the scattering vectors are aligned. In this manner, the sensitivity to overlay among the layers corresponding with the predetermined subset of scattering vectors is enhanced.

In general, an overlay metrology target may include 1D-periodic structures, i.e., with periodicity in one direction and constant in the other, 2D periodic structures, i.e., periodic in two directions, or any combination thereof. For 2D-periodic targets, the two directions of periodicity may or may not be perpendicular to each other. Moreover, the pitch of each of the constituent structures may be the same or different.

By estimating overlay based on the variations of measured intensity associated with each diffraction order, there is no requirement for any specific periodicity or symmetry among the overlay structures comprising the overlay metrology target. Thus, some or all of the overlay structures may not be periodic. For example, the overlay metrology target may be 1D-periodic in one direction and variable but aperiodic in another direction. In another example, the some or all of the overlay structures may be asymmetrical.

In another further aspect, a value of a shape parameter of any of the structures comprising the metrology target is estimated based on a fitting analysis of the detected intensities of the diffraction orders with a measurement model. In some examples, the estimation of overlay and the estimation of one or more shape parameter values are performed simultaneously.

In some examples, the measurement model is a physically based model of the geometry and of the scattering of x-ray radiation by the overlay metrology target. In this approach, a parametric model is developed to describe the structures and materials comprising the metrology target, including the parameters of interest. The values of these parameters are estimated by finding the best fit of simulated data to experimental data.

A model building and analysis engine described in U.S. Patent Publication No. 2014/0019097 by Bakeman et al., which is incorporated herein by reference in its entirety, can be used to create models of samples incorporating geometric and material properties. The models can be used to produce optical and x-ray simulations. In some examples, optical simulations are based on rigorous coupled-wave analysis (RCWA) wherein Maxwell's equations are solved to calculate optical signals such as reflectivities for different polarizations, ellipsometric parameters, phase change, etc. X-ray scattering simulations can be based upon x-ray form factors illustrated in equation (4), $$F(\vec{q}) = \int \rho(\vec{r}) e^{-i\vec{q}\cdot\vec{r}} d\vec{r} \qquad (4)$$

where F is the form factor, q is the scattering vector, and $\rho(r)$ is the electron density of the sample. The x-ray scattering intensity is then given by equation (5), $$I(\vec{q}) = F^*F \qquad (5)$$

as described by R. L. Jones et. al., "Cross Section and Critical Dimension Metrology in Dense High Aspect Ratio Patterns with CD-SAXS," AIP Conference Proceedings, Volume 788, pp. 403-406 (2005), which is incorporated herein by reference in its entirety. In some other examples, a distorted-wave Born approximation is employed.

In some other examples, the measurement model is an input-output measurement model, such as a neural network model, a support vector machine model, a Principal Component Analysis (PCA) model, etc. Additional details regarding input-output measurement models are described in U.S. Patent Publication No. 2016/0003609 by Shchegrov et al., which is incorporated herein by reference in its entirety.

In one example, an edge placement error between layers is estimated based on a measurement of overlay as described herein, and a measurement of a shape parameter based on the intensity measurements within each x-ray diffraction order measured at multiple, different angles of incidence and multiple, different azimuth angles. Edge placement errors (EPE) combine overlay and shape parameter (e.g., CD) errors. In one example, EPE is a difference between a CD value (e.g., width, W, depicted in FIG. 8) and an overlay value (e.g., overlay, D, depicted in FIG. 8). Thus, a measurement of EPE is streamlined by employing the computationally efficient overlay measurement described herein, and using the same intensity measurement data to estimate the CD parameter value.

Figure 10:
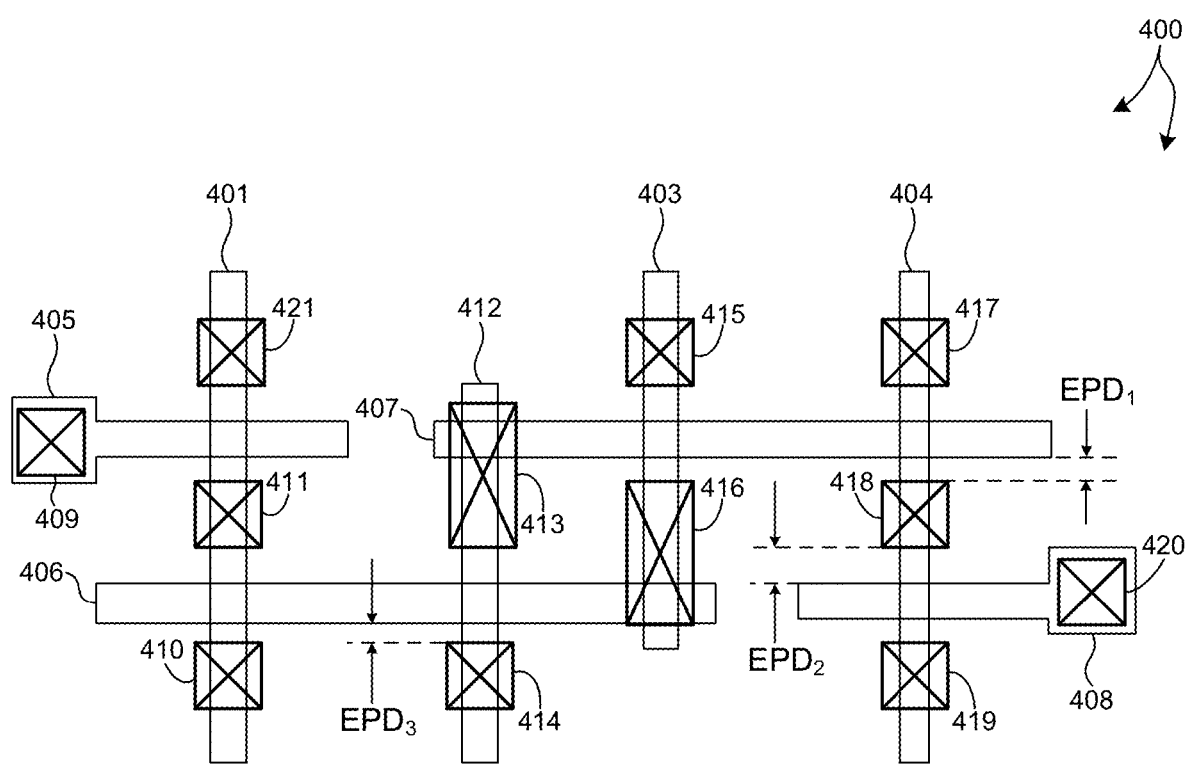
FIG. 10 depicts a top view of device structure 400 that includes active fields 401-404, gates 405-408, and contacts 409-421.

FIG. 10 depicts a top view of device structure 400 that includes active fields 401-404, gates 405-408, and contacts 409-421. FIG. 10 illustrates the edge placement distance, $EPD_1$, between gate 407 and contact 418. FIG. 10 also illustrates the edge placement distance, $EPD_2$, between gate 408 and contact 418 and the edge placement distance $EPD_3$, between gate 406 and contact 414. The edge placement distances must be carefully controlled to ensure high device yield. If the edge placement error associated with any of these edge placement distances is too large, the device will fail. As illustrated in FIG. 10, both overlay errors and CD errors contribute to EPE. For example, EPE results if the layers associated with the contact are misaligned with the layers associated with the gates. Similarly, EPE results if the CD associated with the contact structures deviates from nominal dimensions. For example, contacts 413 and 416 are too large. The result is overlap between each contact and corresponding gate structure and device failure.

Additional details regarding EPE measurements are described in U.S. Patent Publication No. 2016/0003609 by Shchegrov et al., which is incorporated herein by reference in its entirety.

In general, the methods described herein may be applied to many different x-ray diffraction based techniques such as transmission small angle x-ray scattering (TSAXS), grazing incidence small angle x-ray scattering (GISAXS), wide angle x-ray scattering (WARS), x-ray diffraction (XRD), grazing incidence x-ray diffraction (GIXRD), and high resolution x-ray diffraction (HRXRD). In these systems, all diffraction orders which fall upon the detector are collected at once.

For grazing-incidence SAXS implementations, the grazing angle of incidence is adjusted to enable interference fringes of x-ray fields diffracted by gratings at different layers and to optimize penetration depth. Penetration depth may be limited by total internal reflection for grazing incidence angles below the critical angle.

In another further aspect, any of the systems described herein may employ a Bonse-Hart camera to select a specific range of photon energies (Q). In some embodiments, a Bonse-Hart camera includes an analyzer crystal between the sample and the detector. The analyzer crystal has a specific angular acceptance angle which satisfies the Bragg condition. By adjusting the crystal angle, the angular acceptance angle is selected. In one example, a Q range is selected to measure a higher order diffraction peak, for instance, where the intensity modulations are at a higher angular frequency than the lower order peaks. This may enable an overlay measurement with a small number of sample angles. In another example, a Q range is selected to measure a low order diffraction peak, where the overall intensity of the order is greater, to reduce measurement time.

In general, the Bonse-Hart camera may include any suitable selectable analyzer element that limits the transmission of the scattered radiation within a selectable energy range. In one example, the selectable analyzer element is a repeating multilayer film that satisfies the Bragg condition under a certain acceptance angle.

In some embodiments the specimen positioning system that controls the position and orientation of specimen 101 relative to the beam of incident x-ray radiation operates in coordination with a stage system controlling the angle of the analyzer crystal such that the analyzer crystal and the sample are aligned in tandem.

In another further aspect, the overlay metrology target is a design rule target that includes a pitch and CD at the device design rule. In some embodiments, the overlay metrology target is located in-die, instead of a specialized overlay target located in a scribe line area. The methods and systems described herein allow measurement at design rule pitch. This reflects real device overlay more faithfully than existing methods.

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the SAXS detector 116 and the SAXS illumination optics 115 in any manner known in the art. For example, the one or more computing systems 130 may be coupled to computing systems associated with the SAXS detector 116 and the SAXS illumination optics 115, respectively. In another example, any of the SAXS detector 116 and the SAXS illumination optics 115 may be controlled directly by a single computer system coupled to computer system 130.

The computer system 130 may be configured to receive and/or acquire data or information from the subsystems of the system (e.g., SAXS detector 116 and SAXS illumination optics 115, and the like) by a transmission medium that may include wireline and/or wireless portions. In this manner, the transmission medium may serve as a data link between the computer system 130 and other subsystems of the system 100.

Computer system 130 of the metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., signals 126) from a storage medium (i.e., memory 132 or 190) via a data link. For instance, spectral results obtained using a spectrometer of any of SAXS detector 116 may be stored in a permanent or semi-permanent memory device (e.g., memory 132 or 190). In this regard, the measurement results may be imported from on-board memory or from an external memory system. Moreover, the computer system 130 may send data to other systems via a transmission medium. For instance, overlay values 185 determined by computer system 130 may be stored in a permanent or semi-permanent memory device (e.g., memory 190). In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 3, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some embodiments, a scatterometry analysis as described herein is implemented as part of a fabrication process tool. Examples of fabrication process tools include, but are not limited to, lithographic exposure tools, film deposition tools, implant tools, and etch tools. In this manner, the results of a SAXS analysis are used to control a fabrication process. In one example, SAXS measurement data collected from one or more targets is sent to a fabrication process tool. The SAXS measurement data is analyzed as described herein and the results used to adjust the operation of the fabrication process tool.

Scatterometry measurements as described herein may be used to determine characteristics of a variety of semiconductor structures. Exemplary structures include, but are not limited to, FinFETs, low-dimensional structures such as nanowires or graphene, sub 10 nm structures, lithographic structures, through substrate vias (TSVs), memory structures such as DRAM, DRAM 4F2, FLASH, MRAM and high aspect ratio memory structures. Exemplary structural characteristics include, but are not limited to, geometric parameters such as line edge roughness, line width roughness, pore size, pore density, side wall angle, profile, critical dimension, pitch, and material parameters such as electron density, composition, grain structure, morphology, stress, strain, and elemental identification.

Figure 12:
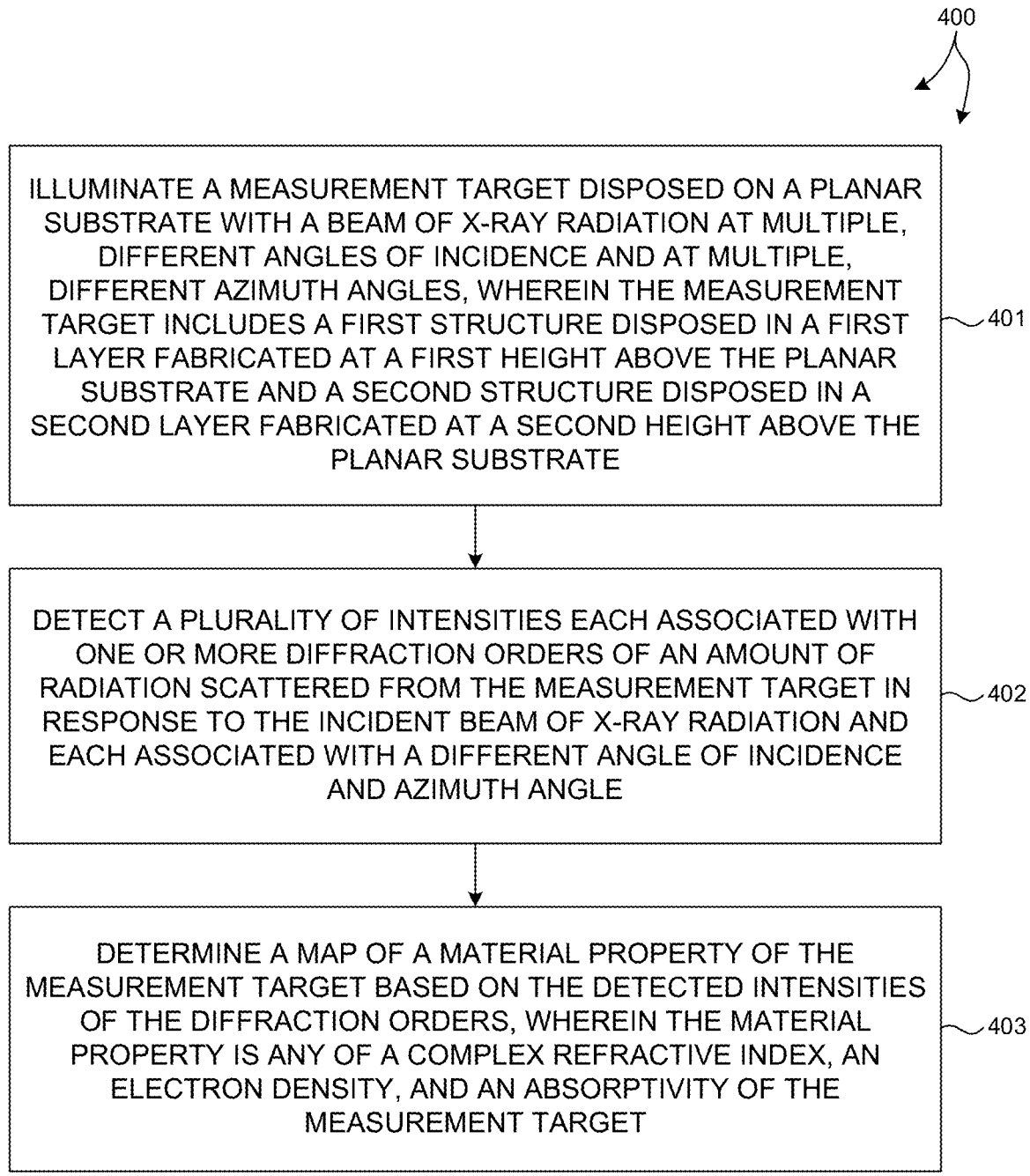
FIG. 12 is a flowchart illustrative of an exemplary method 400 of estimating overlay based on modulations of intensity measurement data as described herein.

FIG. 12 illustrates a method 400 suitable for implementation by metrology system 100 of the present invention. In one aspect, it is recognized that data processing blocks of method 400 may be carried out via a pre-programmed algorithm executed by one or more processors of computing system 130. While the following description is presented in the context of metrology systems 100, 200, and 300, it is recognized herein that the particular structural aspects of metrology systems 100, 200, and 300 do not represent limitations and should be interpreted as illustrative only.

In block 401, a measurement target disposed on a planar substrate is illuminated with a beam of x-ray radiation at multiple, different angles of incidence and at multiple, different azimuth angles. The measurement target includes a first structure disposed in a first layer fabricated at a first height above the planar substrate and a second structure disposed in a second layer fabricated at a second height above the planar substrate.

In block 402, a plurality of intensities is detected. Each of the detected intensities is associated with one or more diffraction orders of an amount of radiation scattered from the measurement target in response to the incident beam of x-ray radiation and each of the detected intensities is associated with a different angle of incidence and azimuth angle.

In block 403, a value of overlay between the first and second structures is estimated based on modulations in the plurality of intensities within each of the one or more x-ray diffraction orders at the multiple, different angles of incidence and the multiple, different azimuth angles.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology systems described herein may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from imaging or structures under measurement.

Various embodiments are described herein for a semiconductor processing system (e.g., a metrology system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, XRF disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
an x-ray illumination source configured to illuminate a measurement target disposed on a planar substrate with a beam of x-ray radiation at multiple, different angles of incidence and at multiple, different azimuth angles, wherein the measurement target includes a first structure disposed in a first layer fabricated at a first height above the planar substrate and a second structure disposed in a second layer fabricated at a second height above the planar substrate;
an x-ray detector configured to detect a plurality of intensities each associated with one or more diffraction orders of an amount of radiation scattered from the measurement target in response to the incident beam of x-ray radiation and each associated with a different angle of incidence and azimuth angle; and
a computing system configured to:
estimate a value of overlay between the first and second structures based on modulations in the plurality of intensities within each of the one or more x-ray diffraction orders at the multiple, different angles of incidence and the multiple, different azimuth angles.

2. The metrology system of claim 1, wherein the estimating of the value of overlay involves a parameterization of the intensity modulations of common orders such that a low frequency shape modulation is described by a set of basis functions and a high frequency overlay modulation is described by an affine-circular function that includes a parameter indicative of the overlay.

3. The metrology system of claim 1, wherein the computing system is further configured to:
estimate a value of a shape parameter of any of the first and second structures based on a fitting analysis of the detected intensities of the diffraction orders with a measurement model.

4. The metrology system of claim 1, wherein the first structure is spatially periodic in at least one direction parallel to a planar surface of the planar substrate.

5. The metrology system of claim 1, wherein the x-ray illumination source illuminates the measurement target with the beam of x-ray radiation at the multiple, different angles of incidence and the multiple, different azimuth angles, simultaneously.

6. The metrology system of claim 1, wherein the x-ray illumination source and the x-ray detector are arranged as elements of any of a transmission small angle x-ray scattering (TSAXS) system, a grazing incidence small angle x-ray scattering (GISAXS) system, a wide angle x-ray scattering (WAXS) system, an x-ray diffraction (XRD) system, a grazing incidence x-ray diffraction (GIXRD) system, a high resolution x-ray diffraction (HRXRD) system.

7. The metrology system of claim 1, wherein the measurement target is a design rule target.

8. The metrology system of claim 1, wherein the measurement target is disposed in-die.

9. The metrology system of claim 1, wherein any of the first structure and the second structure is asymmetrical.

10. The metrology system of claim 1, wherein any of the first structure and the second structure is not periodic.

11. The metrology system of claim 1, wherein the computing system is further configured to:
determine the multiple, different angles of incidence and the multiple, different azimuth angles such that a correlation of the overlay and a shape parameter is minimized.

12. The metrology system of claim 2, wherein the estimating of the value of overlay involves a fitting of the parameterization of the intensity modulations to the measured plurality of intensities.

13. The metrology system of claim 3, wherein the measurement model is any of a physically based measurement model and a signal response metrology model.

14. The metrology system of claim 3, wherein the estimating of the overlay value and the estimating of the value of the shape parameter are performed simultaneously.

15. The metrology system of claim 6, further comprising:
a selectable analyzer element disposed in a path of the radiation scattered from the measurement target before the detector, wherein the selectable analyzer element is configured limit the transmission of the scattered radiation within a selectable energy range.

16. A method comprising:
illuminating a measurement target disposed on a planar substrate with a beam of x-ray radiation at multiple, different angles of incidence and at multiple, different azimuth angles, wherein the measurement target includes a first structure disposed in a first layer fabricated at a first height above the planar substrate and a second structure disposed in a second layer fabricated at a second height above the planar substrate;

detecting a plurality of intensities each associated with one or more diffraction orders of an amount of radiation scattered from the measurement target in response to the incident beam of x-ray radiation and each associated with a different angle of incidence and azimuth angle; and estimating a value of overlay between the first and second structures based on modulations in the plurality of intensities within each of the one or more x-ray diffraction orders at the multiple, different angles of incidence and the multiple, different azimuth angles.

17. The method of claim 16, wherein the estimating of the value of overlay involves a parameterization of the intensity modulations of common orders such that a low frequency shape modulation is described by a set of basis functions and a high frequency overlay modulation is described by an affine-circular function that includes a parameter indicative of the overlay.

18. The method of claim 16, further comprising:
estimating a value of a shape parameter of any of the first and second structures based on a fitting analysis of the detected intensities of the diffraction orders with a measurement model.

19. The method of claim 17, wherein the estimating of the value of overlay involves a fitting of the parameterization of the intensity modulations to the measured plurality of intensities.

20. The method of claim 18, further comprising:
estimating a value of an edge placement error associated with the first and second structures based on the overlay value and the shape parameter value.

* * * * *